United States Patent [19]

Hesketh

[11] Patent Number: 4,874,380
[45] Date of Patent: Oct. 17, 1989

[54] CATHETER RETAINING DEVICE

[75] Inventor: Mark L. Hesketh, Whytelgate, United Kingdom

[73] Assignee: E. R. Squibb and Sons, Inc., Princeton, N.J.

[21] Appl. No.: 142,618

[22] Filed: Jan. 7, 1988

[51] Int. Cl.⁴ .............................................. A61M 5/32
[52] U.S. Cl. .................................... 604/180; 604/338; 128/DIG. 26
[58] Field of Search ............... 604/174, 175, 176, 177, 604/178, 179, 180, 326, 331, 338, 339; 128/DIG. 26, 325, 326, 327

[56] References Cited

U.S. PATENT DOCUMENTS

| | | | |
|---|---|---|---|
| 488,089 | 12/1892 | Roche | 604/174 |
| 978,708 | 12/1910 | Dean | 604/174 |
| 2,402,306 | 6/1946 | Turkel | 604/174 |
| 3,339,546 | 9/1967 | Chen . | |
| 3,682,180 | 8/1972 | McFarlane | 604/174 |
| 4,080,970 | 3/1978 | Miller | 604/174 |
| 4,096,863 | 6/1978 | Kaplan et al. . | |
| 4,360,025 | 11/1982 | Edwards . | |
| 4,378,012 | 3/1983 | Brown . | |
| 4,392,857 | 7/1983 | Berar | 604/179 |
| 4,397,647 | 8/1983 | Gordon | 604/180 |
| 4,416,664 | 11/1983 | Womack | 604/174 |
| 4,099,616 | 10/1987 | Nowak et al. . | |
| 4,516,968 | 5/1985 | Marshall et al. | 604/174 |
| 4,527,559 | 9/1985 | Roxburg et al. | 604/174 |
| 4,533,349 | 8/1985 | Bark | 604/174 |
| 4,551,490 | 11/1985 | Doyle et al. . | |
| 4,571,245 | 2/1986 | Hubbard et al. | 604/179 |
| 4,579,170 | 3/1986 | MacGregor | 604/174 |
| 4,586,919 | 5/1986 | Taheri | 604/179 |
| 4,610,245 | 9/1986 | Biearman | 604/179 |
| 4,617,017 | 10/1986 | Hubbard et al. | 604/179 |
| 4,645,942 | 2/1987 | Weeks . | |
| 4,662,873 | 5/1987 | Lash et al. | 604/179 |
| 4,683,882 | 8/1987 | Laird | 604/179 |
| 4,699,616 | 10/1987 | Nowak et al. | 604/180 |
| 4,717,385 | 1/1988 | Cameron et al. . | |

Primary Examiner—John D. Yasko
Attorney, Agent, or Firm—Donald J. Barrack; Robert E. Lee, Jr.

[57] ABSTRACT

A releasable catheter retaining device is mounted on a pad of medical grade skin adhesive material. The device has a flange with a central hole, and a post extends from a surface of the flange opposite to the pad. An elongated tab extends from the post, there being a slot in the post for receiving the free end of the tab. With this arrangement, the tab can be passed through the slot after encircling a catheter which extends through the hole, in order to grip the catheter and to retain it in position.

5 Claims, 3 Drawing Sheets

CATHETER RETAINING DEVICE

BACKGROUND OF THE INVENTION

The present invention relates to a catheter retaining device.

Catheters for withdrawing or draining body fluids are used in a wide variety of medical and surgical situations. Catheters are tubular and are frequently made of rubber or synthetic rubber. They vary in overall diameter and wall thickness. To hold a catheter in position on the body of a patient, some clamping force must be applied to the catheter. Known catheter retaining devices are designed particularly for use with a narrow size range of catheter. Catheter retaining devices which clamp the tube are normally not satisfactory for use both with a relatively large outside diameter, large wall thickness catheter and with a thin-walled catheter because the clamping force tends to deform the thin wall thickness catheter and to close off the passage therein.

The present invention aims to provide a versatile releasable catheter retaining device.

SUMMARY OF THE INVENTION

According to the present invention, there is provided a releasable catheter retaining device comprising a flange having a central hole therein and mounted on a pad of medical grade skin-compatible adhesive material, the flange being made in one piece with a post extending from the side of the flange opposite to the pad and with an elongated tab extending from the post, there being a slot in the post for receiving the free end of the tab, the arrangement being such that the tab can be passed through the slot after encircling a catheter which extends through the hole, so gripping the retaining the catheter in position.

According to the preferred embodiment, the post has a resilient detent associated with the slot, the detent being movable between a first position in which it grips the tab and second position in which the tab is released.

According to a particular embodiment of the invention, the detent may be made in one piece with the post, flange and tab, and all these parts may be made of a synthetic plastics material for examples, ethylene vinyl acetate or low density polyethylene.

In a particularly preferred embodiment of the invention, a notch or groove extends across the width of the tab at or near the root of the tab, that is to say where the tab joins the post. This notch or groove increases the range of movement that the tab can make relative to the post, and so facilitates bending the tab relative to the post to a position where it closely encircles a small outside diameter catheter.

The pad of medical grade skin compatible adhesive material may be that described by Chen in U.S. Pat. No. 3,339,546 and Doyle, et al. in U.S. Pat. No. 4,551,490. Other similar materials are also suitable.

DETAILED DESCRIPTION OF THE PREFERRED EMBODIMENT

Figure 1:
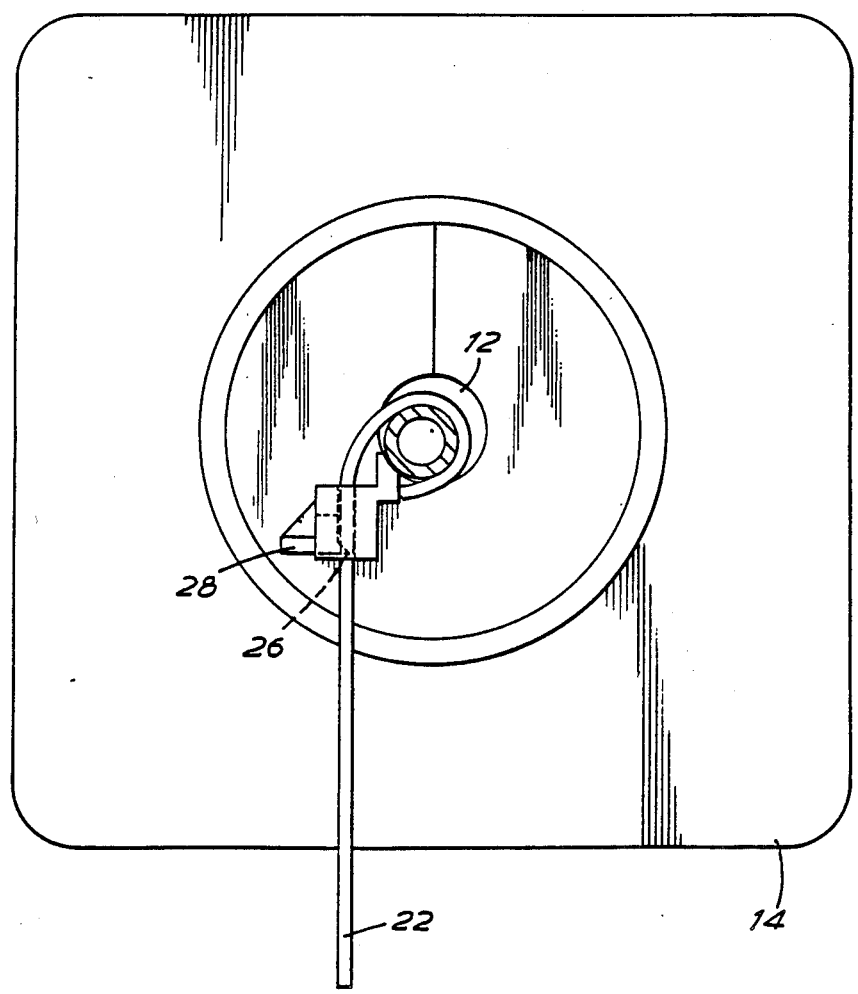
FIG. 1 is a front view of a releasable catheter retaining device according to an example of the invention.
Figure 3:
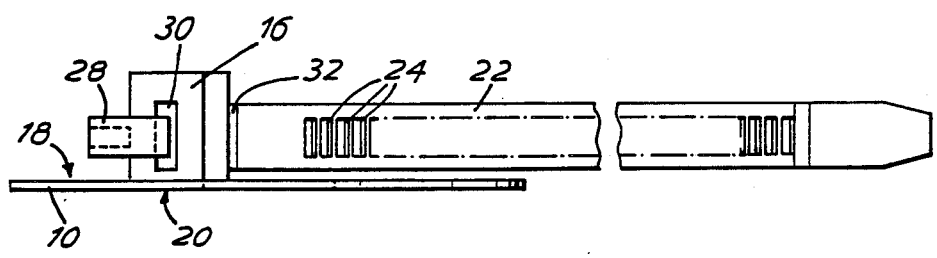
FIG. 3 is a side view corresponding to FIG. 2.
Figure 4:
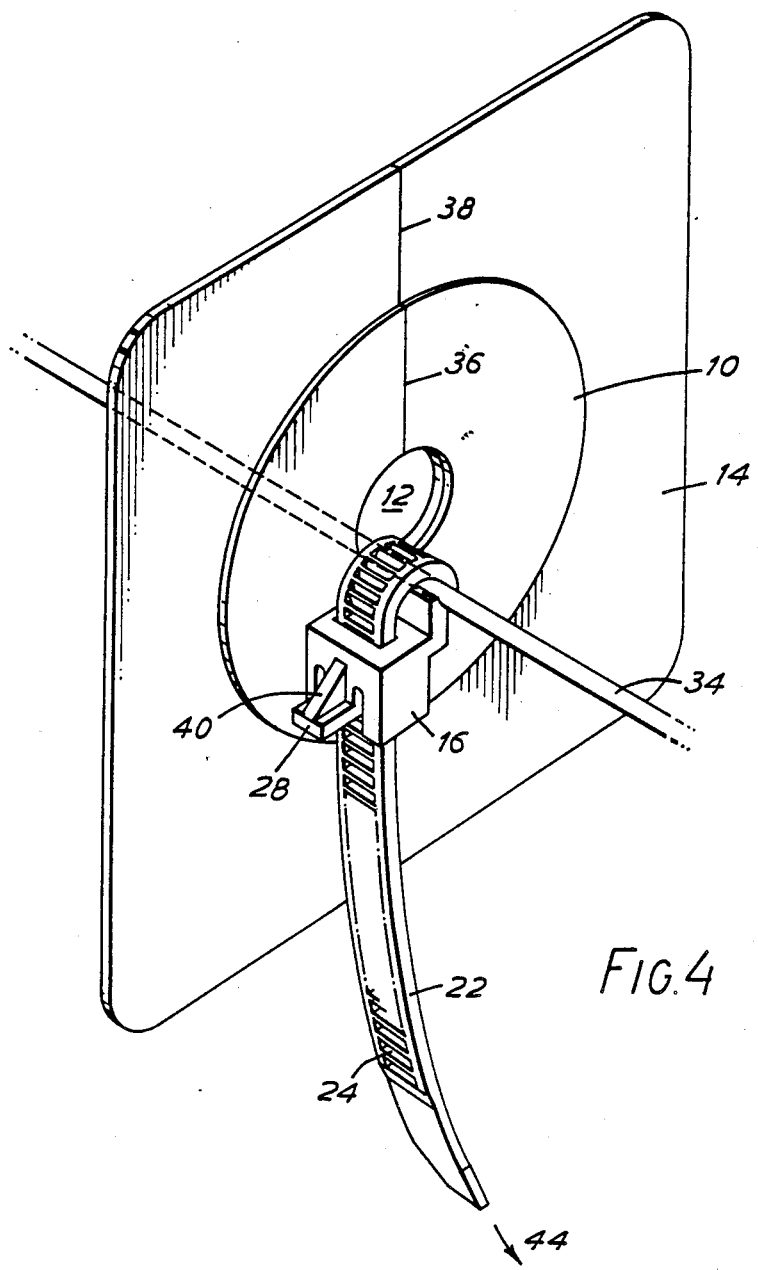
FIG. 4 is a perspective view of the device illustrating the retention of small diameter catheter.

Referring to FIGS. 1 and 4, the illustrated device includes a flange 10 having a central hole 12 therein. The flange is mounted in face to face manner on a pad 14 of medical grade skin compatible adhesive material. The flange 10 is made in one piece with a post 16. The post 16 extends from the surface 18 of the flange which is the opposite surface to that surface (20, FIG. 3) to which the pad 14 is attached. Made in one piece with the post 16 is an elongated tab 22 having a series of depressions therein. These depressions, in use, serve as ratchet teeth 24, operating with the detent tooth 26, FIG. 1, on the detent 28.

The post 16 has a slot 30 therethrough, through which the elongated tab 22 can be threaded as illustrated in FIG. 4. At the root of the tab 22 there is a notch or cross groove 32. This increases the range of movement of the tab 22 so that it can closely encircle even a small outside diameter small wall thickness catheter such as is illustrated at 34 in FIG. 4.

Figure 2:
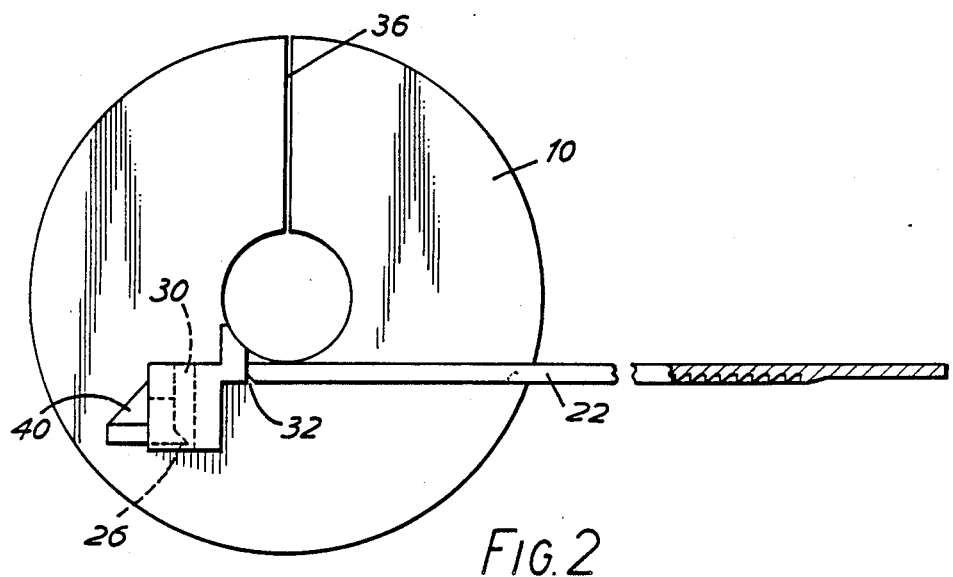
FIG. 2 is a front view of the flange, post, tab, and detent forming part of the device of FIG. 1.

The flange 10 may have a radial slit therein extending from the hole 12 to its periphery. The slit is shown at 36 in FIGS. 2 and 4. Its purpose is to enable a catheter to be introduced into the hole 12 without the need to thread the whole length of the catheter through the hole. A like slit may be included for a like purpose in the pad of medical grade adhesive 14 this slit being indicated at 38.

The flange, post, tab, and detent may be molded integrally from synthetic plastics material and a stiffening bar 40, FIG. 3, may be included connecting a part of the detent to the post. Pressure on the detent in the direction indicated at 42 in FIG. 2 lifts the detent tooth 26 out of engagement with one of the recesses 24 and allows the elongated tab to be withdrawn and the catheter to be released. Conversely, after the tab 22 has been threaded through the slot 30, a longitudinal pull in the direction 44, FIG. 4, enables the elongated tab 22 to be tightened to any extent desired around the catheter which it encircles. With this arrangement, irrespective of whether a catheter of outside diameter 10 mm or more, or a small catheter of outside diameter of 2 or 3 mm is employed, one can achieve a satisfactory clamping of the catheter without an undesired deformation of its wall and occlusion of its internal passage.

It will be appreciated that modifications may be made without departing from the invention. For example, the flange 10 need not be circular as illustrated. Instead of having a central hole, a closed line of weakening could be provided so that the user could punch out a central portion so providing the necessary hole for the catheter. While reference has been made to an upstanding post 16, any structure providing an attachment point for an elongated tab and a slot through which the free end of the tab may be inserted could be employed. Detents of other types or shapes than that illustrated could be employed.

I claim:

1. A releasable catheter retaining device comprising a substantially planar flange having a central hole therein and mounted on a pad of medical grade skin-compatible adhesive material, the flange being made in one piece with a post extending from the side of the flange opposite to the pad and with an elongated tab extending from the post, there being a slot in the post for receiving the free end of the tab, the arrangement being such that the tab can be passed through the slot after encircling a catheter which extends through the hole, and wherein the post has a resilient detent associated with the slot, the detent having a detent tooth, the detent and tooth being movable in a plane parallel to the plane of the flange between a first position in which the detent tooth grips the tab in the slot and a second position in which the tooth is disengaged from the tab and at least partially withdrawn from the slot and the tab is released.

2. The device of claim 1 in which there is a notch or groove extending across the width of the tab or near the root of the tab, to increase the range of movement of the tab relative to the post.

3. The device of claim 1 in which there is a notch or groove extending across the width of the tab or near the root of the tab, to increase the range of movement of the tab relative to the post.

4. The device of claim 3 in which the detent is made in one piece with the post, flange, and tab, all these parts being made of a synthetic plastics material.

5. The device of claim 4 in which there is a notch or groove extending across the width of the tab or near the root of the tab, to increase the range of movement of the tab relative to the post.

* * * * *